United States Patent [19]

Stoutamire

[11] Patent Number: 4,570,017
[45] Date of Patent: Feb. 11, 1986

[54] PREPARATION OF OPTICALLY-ACTIVE (MIXED) ANHYDRIDES AND ACIDS

[75] Inventor: Donald W. Stoutamire, Modesto, Calif.

[73] Assignee: Shell Oil Company, Houston, Tex.

[21] Appl. No.: 593,154

[22] Filed: Mar. 26, 1984

Related U.S. Application Data

[63] Continuation-in-part of Ser. No. 459,012, Jan. 18, 1983.

[51] Int. Cl.$^4$ .................... C07C 53/134; C07C 57/30
[52] U.S. Cl. .................................. 562/496; 562/426; 562/429; 562/431; 562/464; 562/527; 260/548; 568/301
[58] Field of Search ............... 562/496, 426, 429, 431, 562/464, 527; 260/548; 568/301

[56] References Cited

FOREIGN PATENT DOCUMENTS 0057092  4/1982  European Pat. Off. ............ 562/401

OTHER PUBLICATIONS

CA, 58:12479f (1963).
Organic Reactions, pp. 124–127; R. Adams, editor; John Wiley & Sons, Inc., N.Y., N.Y. (1946).

Primary Examiner—Paul J. Killos

[57] ABSTRACT

A process for the preparation of an optically-active (mixed) anhydride of an alpha-chiral (optically-active) carboxylic acid by treating a non-symmetrical ketene with a carboxylic acid in the presence of an optically-active (chiral) tertiary amine catalyst. Hydrolysis of the resulting (mixed) anhydride yields the optically-active acid corresponding to the non-symmetrical ketene.

30 Claims, No Drawings

PREPARATION OF OPTICALLY-ACTIVE (MIXED) ANHYDRIDES AND ACIDS

CROSS-REFERENCE TO RELATED APPLICATIONS

This application is a continuation-in-part of Ser. No. 459,012, filed Jan. 18, 1983.

BACKGROUND OF THE INVENTION

1. Field of the Invention

The present invention is directed to processes for the preparation of optically-active (mixed) anhydrides and acids.

2. Description of the Prior Art

Carboxylic acids are of interest because they or their esters, salts and the like often have useful effects in biological systems, e.g. as herbicides, plant growth regulators, analgesics, antipyretics, antiinflammatory agents, or also in the form of esters as insecticides and miticides. In particular, the optically-active acids and their esters, salts and the like usually have some different effects in biological systems from those of their enantiomers. Although a variety of methods to obtain optically-active acids are known, these acids are usually obtained by classical resolution, which is time consuming and not practical on a large scale.

The present process provides a process for preparing optically-active acids or (mixed) anhydrides in high yield by a direct synthesis method, avoiding the cumbersome and expensive classical resolution of the optically-active acids.

SUMMARY OF THE INVENTION

The present invention is directed to a process for the preparation of an optically-active (mixed) anhydride of an alpha-chiral (optically-active) carboxylic acid or a mixture enriched therein, which comprises treating a non-symmetrical ketene with a racemic or optically-active (chiral or achiral) carboxylic acid reactant in the presence of an optically-active (chiral) tertiary amine catalyst. Depending on the reactants selected, the product (mixed) anhydride of the process of the invention is a (mixed) anhydride enriched in one of its optically-active diastereomers or enriched in one enantiomer pair, the enrichment being over an equimolar amount of diastereomer(s) expected from the reaction of an equimolar amount of a non-symmetrical ketene with a racemic or optically-active carboxylic acid.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. The solvent is preferably an aromatic solvent, especially toluene.

Any non-symmetrical ketene is useful (provided it does not contain substituent groups which form other stable reaction products with the carboxylic acid. The non-symmetrical ketene has the formula I

wherein $R^1$ and $R^2$ each independently is a different alkyl, aralkyl, alkoxy, aryloxy, alkylthio, alkylsulfonyl, arylthio or arylsulfonyl group containing from 1 to 10 carbon atoms or a cycloalkyl group containing 3 to 7 ring carbon atoms, or $R^2$ is also an alkenyl or alkynyl group containing 2 to 10 carbon atoms; a naphthyl group, a phenyl group, a heterocyclic group containing 5 or 6 ring atoms, one of which is oxygen, sulfur or nitrogen, and the remainder are carbon atoms; or is an amino group disubstituted by acyl or alkyl containing up to 10 carbon atoms or a phenyl group; or $R^1$ and $R^2$, when taken together with the carbon atom to which they are attached, form a non-symmetrical cycloalkyl group containing 4 to 7 ring carbon atoms and 4 to 14 carbon atoms. The $R^1$ and $R^2$ groups can be optionally substituted by one or more of halogen atoms having an atomic number of from 9 to 35, alkyl or haloalkyl containing 1 to 4 carbon atoms, alkenyl or haloalkenyl containing 2 to 4 carbon atoms, haloalkoxy or alkoxy of 1 to 4 carbon atoms, haloalkylthio or alkylthio of 1 to 4 carbon atoms or equivalent kinds and sizes of substituents which may contain the same or greater carbon number.

One embodiment of non-symmetrical ketenes used in the process of the invention is that which is used in making pyrethroid esters, including those esters having an acid moiety described in U.S. Pat. Nos. 4,062,968 or 4,199,595. Examples of such ketenes include those having the formula I in which $R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine, and the alkyl groups contain 1 or 4 carbon atoms.

Of particular interest as non-symmetrical ketene reactants because their pyrethroid esters are usually highly pesticidally active are those ketenes having the formula I in which $R^1$ is isopropyl; $R^2$ is a phenyl group para-substituted by halogen, alkyl, haloalkoxy in which the halogen, e.g. chlorine or fluorine and the alkyl contain 1 to 4 carbon atoms, e.g. methyl.

For example, the non-symmetrical ketene is (4-chlorophenyl)isopropylketene, (4-(difluoromethoxy)-phenyl)isopropylketene, or (4-(trifluoromethyl)-3-chlorophenyl)(benzyloxycarbonyl)amino)isopropylketene, and the like.

Any racemic or optically-active carboxylic acid reactant which does not interfere with the reaction can be used. For example, the carboxylic acid is an acyclic, carbocyclic, aromatic or heterocyclic acid containing up to about 20 carbon atoms. Non-limiting examples include acids such as butyric, benzoic, cyclohexanoic, picolinic or furoic acid. Preferably, the acid is an alkanoic acid or aromatic acid containing from 1 to about 8 carbon atoms, such as formic, acetic, propionic, butyric, pentanoic, hexanoic, heptanoic, octanoic, benzoic, phenylacetic and the like. Because of their availability and ease of recovery, suitable acids are alkanoic acids containing from 1 to 4 carbon atoms. Formic or acetic acids are preferred.

The optically-active (chiral) tertiary amine catalyst is any optionally-substituted alkyl, cycloalkyl, aromatic or heterocyclic dior polyamine containing up to 40 carbon atoms (including polymers and copolymers and amine salts and the like), which will not interfere with the reaction. The amine is preferably a moderate to weakly basic amine. The optically-active amines, polymers and copolymers are conventional kinds of materials known in the art and can be prepared by known methods except for certain novel ketene reaction products discussed below. For example, numerous optically-active di- and polyamines are specifically disclosed in Newman, P., "Optical Resolution Procedures for Chemical Compounds", Vol. 1, Amines and Related Compounds, Optical Resolution Information Center, Manhattan College, Riverdale, N.Y., Library of Congress Catalog Card No. 78-61452. This reference also discloses optically-active mono-, di- and polyamines which can be polymerized and co-polymerized by known procedures to form optically-active polymeric amines for use in the invention.

One embodiment of the optically-active amine catalyst comprises a substituted optically-active amino acid which is preferably any acyclic, carbocyclic, aromatic or heterocyclic amino acid containing up to 20 carbon atoms, preferably up to 10 carbon atoms, additionally substituted by a moderate to weakly basic nitrogen base substituent or is the reaction product thereof with one or three moles of a ketene. Suitable nitrogen-base substituents include optionally substituted nitrogen-heterocyclic groups or amino groups, each optionally substituted by alkyl or cycloalkyl groups containing 1 to 6 carbon atoms or by optionally substituted phenyls. Other optional substituents include hydroxy, carbonyl, thiol, alkyl, alkoxy, amino, alkylthio, amido and the like. Examples of nitrogen-heterocyclic groups include thiazolyl, imidazolyl, pyrrolyl, benzopyrrolyl and the like.

Non-limiting examples of the optically-active catalyst include beta-aminoalanine, ornithine, canavanine, anserine, kynurenin, mimosine, cystathionine, ephedrin, acylated ephedrin, histidinol, citrulline, carbamoylserine, cinchonine, quinine or acylated quinuclidinyl alcohols.

Another embodiment of amine catalysts are the heterocyclic amines and polymers of heterocyclic amines. Non-limiting examples include di- and polyaziridines, polymers of acryloylcinchonines alone or with N,N-diacryloylhexamethylenediamine, di- and poly(iminoisobutylethylene), polymers of (N-benzyl-2-pyrrolidinylmethyl ester) with acrylate or a lower alkanoic acid, and like materials.

In another embodiment of the invention, the catalyst is an optically-active histidine-containing peptide catalyst; or is a histidine-containing di- or polypeptide; in which at least one of the histidinyl free N-H and free COOH groups is modified with a protecting group into the form of an amide (or acid addition salt thereof) and an ester group respectively; or the reaction product of one mole of a histidine or a histidine-containing mono-, di- or polypeptide with from about one mole to about three moles of a ketene per mole of histidine group.

The di- or polypeptide is linear or cyclic. These peptides usually contain from about 2 up to about 16 peptide units, preferably 2 to 4 peptide units. Nitrogen-substituted amino acids, including these histidine-containing di- and polypeptides, are prepared by conventional peptide synthesis, for example, as in Greenstein, J. P. and M. Winitz, "Chemistry of the Amino Acids", John Wiley & Sons, Inc., New York, 1961.

The peptides of the histidine-containing catalyst are preferred, especially in the cyclic dipeptide form. The di- or polypeptides may also contain alanine, and those prepared with alanine, phenylalanine or alanine derivatives, are preferred.

In one embodiment of the invention, the asymmetric carbon atoms in the histidine-containing peptide, catalyst have the D configuration. Choice of chirality of the catalyst can be made so as to provide the chirality desired in the product.

Functional groups in the amino acid catalyst can contain protecting groups; any conventional amino acid protecting group known in the art can be used. For example, the protecting group is an organic acid in the case of the free N-H or an alcohol in the case of the free COOH. Any organic acid and alcohol which will not interfere with the reaction can be used as the protecting group. Preferably, the protecting group is an other amino acid. Any amino acid can be used, but, preferably, the amino acid is non-heterocyclic and is a monoamino or diamino-alkanoic or aralkanoic acid, such as alanine, phenylalanine, glutamic acid, glycine and the like.

The acid addition salts of the amine catalyst are formed with any acid that will not interfere with the reaction. Suitable inorganic acids include hydrohalogenic acids, such as hydrochloric or hydrobromic; sulfur acids, such as sulfuric or toluenesulfonic; and phosphorus acids, such as phosphoric or phenylphosphonic; and organic acids, such as oxalic acid and the like, are also suitable to form the salts.

When preparing the di- or polypeptide catalyst also having an alanine (containing moiety), it is prepared from alanine or its derivatives; this includes alanine, beta-aminoalanine, beta-phenylalanine, 3,4-dihydroxphenylalanine and the like. When preparing the catalyst from a histidine (containing moiety), it is preferably histidine, 3-methylhistidine, 3-ethylhistidine, 3-propylhistidine, 3-benzylhistidine, 1-methylhistidine, 1-ethylhistidine, 1-propylhistidine, 1-benzylhistidine, and the like. Preferably, the catalyst is a cyclic dipeptide containing a histidine moiety and an alanine moiety.

The adducts (reaction products) with a ketene are prepared to contain from about one mole to about three moles of a ketene per mole of nitrogen-based amino acid unit. Obviously, it is preferable to form the adduct in situ with the non-symmetrical ketene reactant of the process, which is described below under process conditions. However, treatment of the optically-active catalyst with about 1.1 to 5 moles of a ketene, preferably in the absence of a solvent or any solvent used in preparing the ketene, is suitable. The ketene may also be a symmetrical ketene or ketene itself.

Non-limiting examples of the optically-active histidine-containing catalyst include histidine, alpha-methylhistidine, 1-methylhistidine, 3-methylhistidine, cyclo(histidyl-histidine), (benzyloxycarbonylalanyl)histidine methyl ester, cyclo(alanyl-histidine), cyclo(beta-phenylalanyl-histidine), histidine methyl ester hydrochloride, histidine ethyl ester dihydrochloride, anserine, cyclo(valyl-histidine), glycylhistidine, cyclo(phenylalanyl-glycyl-histidine), cyclo(leucyl-histidine), cyclo(homophenylalanyl-histidine), cyclo(phenylalanyl-methylhistidine), N-alpha-(beta-naphthoyl)histidine, histidyl-alanine, histidyl-phenylalanamide hydrochloride, histidyl-phenylalanine, cyclo(histidyl-proline), cyclo(glycyl-histidine) in a free or protected form or a reaction product of these materials with a ketene. Also, cyclo(beta-phenylalanyl-histidine) adduct with (4-(difluoromethoxy)phenyl)isopropylketene, histidine adduct with ketene, cyclo(glycyl-histidine) adduct with (4-(difluoromethoxy)phenyl)isopropylketene, and histidylalanine adduct with dimethylketene and the like.

In one embodiment of the invention, the catalyst has the formula

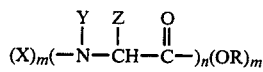

wherein X is H, alkyl or

each R is independently alkyl or cycloalkyl of up to 7 carbon atoms, optionally substituted phenyl, benzyl or the like, each of the n units of

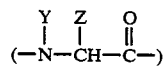

is independently substituted in which Y is hydrogen, acyl, alkyl or aralkyl of up to 10 carbon atoms; Z is the residue of common amino acids that do not interfere in the process of the invention including benzyl, 3-carboxypropyl, 3-aminopropyl, mercaptomethyl, 4-hydroxybenzyl, imidazol-4-ylmethyl; each m is 0 or 1, n is 1 to 16; when each m is 0, the catalyst has a cyclic structure denoted by the dotted line; with the proviso that at least one histidine or substituted histidine unit is included in the catalyst; or the reaction products of the above catalysts with from about one to about three moles of a ketene.

When the catalysts are prepared by conventional methods in the presence of water, they can, if solid, also contain solvent (e.g. water) of crystallization. The optically-active, nitrogen-based amino acid, e.g., histidine-containing peptide, catalyst of the invention, thus, includes the presence or absence of solvent (e.g. water) of crystallization when solid.

The amount of catalyst can vary. For example, it can be used in the range of from about 0.1 to about 5 mole percent based upon the weight of the carboxylic acid reactant present, preferably about 1.5 to about 2.5 mole percent.

A second embodiment of the invention is a process for the preparation of an optically-active carboxylic acid which comprises treating a non-symmetrical ketene with an optically-active or achiral carboxylic acid reactant in the presence of an optically-active tertiary amine catalyst followed by separation of the resulting (mixed) anhydride diastereomers and hydrolysis of the resulting (mixed) anhydride diastereomer to the optically-active acid corresponding to the non-symmetrical ketene.

The non-symmetrical ketene, carboxylic acid reactant, solvent (if any) and amine catalyst are those described above.

It is desirable, however, that the non-symmetrical ketene and the carboxylic acid be of dissimilar molecular weights so that upon hydrolysis the desired optically-active carboxylic acid can be separated and recovered by conventional techniques, such as distillation, extraction, crystallization and the like. The diastereomers are separated by conventional techniques used for separating diastereomers, e.g. chromatographic separation and the like.

The hydrolysis is conducted in the presence of water or source of water and under conditions conventional for hydrolysis of anhydrides. Conveniently, the hydrolysis is conducted with dilute mineral acid at about ambient temperature or above. If a solvent is used in the hydrolysis, it is conveniently any used in the step of forming the (mixed) anhydride.

In forming the (mixed) anhydride, the molar ratio of the starting materials can vary. For example, the molar ratio of the nonsymmetrical ketene to carboxylic acid reactant is from about 10 to 1 to about 1 to 10, and preferably from about 5 to 1 to about 1 to 5. However, it is desirable to have either equivalent amounts (1:1) of the starting materials or a molar excess of acid to ketene of from about 1 to 1.1 to about 1 to 1.5.

In forming the (mixed) anhydride, the temperature of the reaction as well as the pressure can vary. At normal pressures, the temperature is conveniently from about 0° C. to about 50° C., more or less. Ambient temperatures of about 15° C. to about 35° C. are convenient.

In forming the (mixed) anhydride, the process is preferably conducted by adding the carboxylic acid to the catalyst maintained under nitrogen. To a stirred, single phase of this catalyst-acid mixture is added the non-symmetrical ketene. The resulting (mixed) anhydride is optionally hydrolyzed with or without intermediate purification and/or separation.

The process of the invention is useful to prepare an optically-active acyclic, alicyclic, aromatic or heteroaromatic acid. Preferably, the acid has the formula II

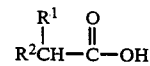

wherein $R^1$ and $R^2$ are different and each independently is an alkyl, aralkyl, alkoxy, aryloxy, alkylthio, alkylsulfonyl, arylthio or arylsulfonyl group containing from 1 to 10 carbon atoms or a cycloalkyl group containing 3 to 7 ring carbon atoms, or $R^1$ and $R^2$, when taken together with the carbon atom to which they are attached, form a nonsymmetrical cycloalkyl group containing 4 to 7 ring carbon atoms; $R^2$ is also an alkenyl or alkynyl containing from 2 to 10 carbon atoms, a naphthyl group, a phenyl group, a heterocyclic group containing 5 or 6 ring atoms, one of which is oxygen, sulfur or nitrogen, and the remainder are carbon atoms or is an amino group disubstituted by acyl or alkyl of up to 10 carbon atoms or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4 carbon atoms, haloalkoxy or alkoxy group of 1 to 4 carbon atoms, haloalkylthio or alkylthio group of 1 to 4 carbon atoms or equivalent kinds of substituents.

One embodiment of acids are pyrethroid acids, including those of U.S. Pat. Nos. 4,062,968 or 4,199,595. Examples of such acids include those having the formula II in which $R^1$ is isopropyl or cyclopropyl, optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine and the alkyl groups contain 1 or 4 carbon atoms. For example, the acid halide is isopropyl-(4-chlorophenyl)acetic, isopropyl-(4-(difluoromethoxy)phenyl)acetic, or isopropyl-((4-(-trifluoromethyl)-3-chlorophenyl)(benzyloxycarbonyl)amino)acetic, and the like.

Preferably, in formula II, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position. especially useful are 4-chlorophenyl, 4-(difluoromethoxyphenyl, 4-methylphenyl, 4-tert-butylphenyl and the like. $R^2$ is preferably 4-chlorophenyl.

The non-symmetrical ketenes are generally known in the art or are novel. Ketenes used in the present invention can be prepared by treating the corresponding acid halide with a tertiary amine.

The tertiary amine can be any alkyl, aryl or heterocyclic nitrogen base including mono- or polyamines and the like. Preferably, the tertiary amine is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom, such as trimethylamine, triethylamine, tri-n-propylamine, pyridine and the like. It desirably contains three alkyl groups of 1 to 4 carbon atoms, for example: trimethylamine, tri-n-propylamine, and especially triethylamine or trimethylamine.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. Tetrahydrofuran and dioxane are also useful.

In the preparation of the non-symmetrical ketene, the molar ratio of the starting materials can be varied widely. For example, the molar ratio of acid halide to base is from about 10:1 to about 1:10, and preferably from about 5:1 to about 1:5. However, it is desirable to have a molar excess of base to acid halide. Therefore, a molar ratio of acid halide to base is desirably from about 1:1 to about 1:5 and conveniently from about 1:1.2 to about 1:2.

In the preparation of the non-symmetrical ketene, the temperature can be varied widely. At normal pressure, for example, the temperature of reaction can be varied but is preferably, for example, from about 10° C. to 40° C. more or less, although higher temperatures of about 75° C. to about 95° C. have been found very useful.

Separation and recovery of the product non-symmetrical ketene are achieved by conventional methods, including crystallization and the like.

This process is useful for preparing non-symmetrical ketenes from any acid halides which do not contain substituted groups which would react with the tertiary amine. For example, the acid halide can be that of an acyclic, alicyclic, aromatic or heteroaromatic acid. Preferably, the acid halide has the formula III

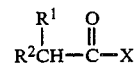

wherein X is the halogen atom, such as chlorine or bromine, $R^1$ and $R^2$ each independently is an alkyl, aralkyl, alkoxy, aryloxy, alkylthio, alkylsulfonyl, arylthio or arylsulfonyl group containing from 1 to 10 carbon atoms or a cycloalkyl group containing 3 to 7 ring carbon atoms, or when taken together with the carbon atom to which they are attached form a non-symmetrical cycloalkyl group containing 4 to 7 ring carbon atoms; $R^2$ is also an alkenyl or alkynyl containing from 2 to 10 carbon atoms, a naphthyl group, a phenyl group, a heterocyclic group containing 5 or 6 ring atoms, one of which is oxygen, sulfur or nitrogen, and the remainder are carbon atoms or is an amino group disubstituted by acyl or alkyl containing up to 10 carbon atoms or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4, haloalkoxy or alkoxy group of 1 to 4 carbon atoms, haloalkylthio or alkylthio group of 1 to 4 carbon atoms or equivalent kinds of substituents.

One embodiment of acid halides are halides of pyrethroid acids, including those of U.S. Pat. Nos. 4,062,968 or 4,199,595. Examples of such acid halides include those having the formula I in which $R^1$ is isopropyl or cyclopropyl, optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine and the alkyl groups contain 1 or 4 carbon atoms. For example, the acid halide is isopropyl-(4-chlorophenyl)acetyl chloride, isopropyl-(4-(difluoromethoxy)phenyl)acetyl chloride, or isopropyl-((-4(-trifluoromethyl)-3-chlorophenyl)(benzyloxycarbonyl)amino)acetyl chloride, and the like.

Preferably, in formula III, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxyphenyl), 4-methylphenyl, 4-tert-butylphenyl and the like. $R^2$ is preferably 4-chlorophenyl. Many of the nonsymmetrical ketenes of the invention are known in the art per se, for example, (4-chlorophenyl)isopropylketene, as in U.S. Pat. No. 4,199,527. Some other non-symmetrical ketenes are believed to be novel, for example, including (4-(difluoromethoxy)phenyl)isopropylketene.

The (mixed) anhydrides of the invention are intermediates to the acids of the invention, which are known analgesics, antipyretics or antiinflammatory agents, as, for example, in U.S. Pat. Nos. 3,686,183, 3,452,079, 4,009,283, 4,335,251 and the like. A variety of (insecticidal and miticidal) esters of the acids of the invention are known in the art, particularly alpha-cyano esters, including those described in *J. Chem. Soc.*, 95. pages 1403–1409 (1909) and in the optical forms, including British Pat. No. 2,014,137 and the like.

Preferably, the product (mixed) anhydride is of formic or especially of acetic acid with an acid selected from S-isopropyl-4-chlorophenylacetic, or S-isopropyl-4-(difluoromethoxy)phenylacetic, which on hydrolysis yields the corresponding acids.

ILLUSTRATIVE EMBODIMENTS

The following embodiments are provided for the purpose of illustrating the invention and should not be regarded as limiting it in any way. The identity of the products was confirmed by infrared and nuclear magnetic resonance spectral analyses as necessary.

Embodiment 1—N-(Benzyloxycarbonyl)-D-phenylalanine

A 15.0 g sample of D-phenylalanine was dissolved in 45 ml of aqueous solution containing 7.26 g of 50% sodium hydroxide. This solution was stirred at 0°–10° C. as 16.3 g of benzyl chloroformate was added rapidly in portions. The resulting reaction was mildly exothermic, and shortly after addition, solids precipitated. An additional 45 ml of water and 3.63 g of 50% sodium hydroxide were added, causing most of the solids to redissolve. The reaction mixture was stirred for 20 minutes and then acidified with 6N hydrochloric acid. The resulting solids were filtered, washed with water and then with hexane, and dried by suction and then under vacuum to give 47 g of white solids. These solids dissolved in ether were washed twice with 1N hydrochloric acid and then with water, dried over MgSO$_4$ and stripped to 35° C. at 2.5 mm Hg to give 27.7 g of the desired product as a colorless oil.

Embodiment 2—N-(Benzyloxycarbonyl)-D-phenylalanine, p-nitrophenyl Ester

A 300 ml three-neck flask with stirrer and dropping funnel was charged under a nitrogen atmosphere with 27 g of the acid of Embodiment 1 above in 135 ml of pyridine, followed by 13.2 g of p-nitrophenol. The resulting solution was cooled to 0° to 10° C. as 14.6 g of phosphorus oxychloride was added. The resulting mixture was warmed to 25° C., stirred for 15 minutes, then poured into 300 ml of ice water. Filtration of the resulting solid, followed by washing with water and drying by suction, gave 33 g of product. This was crystallized from 340 ml of hot ethyl alcohol with chilling to −5° C. The product was filtered, washed with chilled ethyl alcohol, then with hexane, and sucked dry to give 28.7 g of the desired product, m.p. 122.5°–124.5° C., $[\alpha]_D^{23}+24.7$ (c 2.0, dimethylformamide).

Embodiment 3—N-Benzyloxycarbonyl-D-phenylalanyl-D-histidine Methyl Ester

To a stirred solution of 5.0 g of D-histidine methyl ester hydrochloride in 40 ml of methylene chloride was added 4.18 g of triethylamine followed by 8.27 g of the nitrophenyl ester prepared as in Embodiment 2 above. The reaction mixture immediately became bright yellow and solids began to precipitate. The reaction mixture was stirred for 2 hours, then stored overnight at −10° C. The reaction mixture was rewarmed to room temperature, and 0.6 ml of triethylamine was added. Then, 490 mg of the D-histidine methyl ester hydrochloride was added, and stirring was continued for 2 hours. The reaction mixture was washed with 20 ml of water, then twice with 20 ml of 10% ammonium hydroxide, and then twice with 20 ml of water. All the washes were back-extracted serially with 20 ml of methylene chloride, and the combined organic phases were dried with MgSO$_4$ and stripped to 100 ml, filtered through silica, followed by 25 ml of 20% methanol in ethyl acetate. The resulting eluate was stripped to 40 ml and diluted to 120 ml with diethyl ether; the precipitated solid was filtered, washed with diethyl ether, and dried by suction to give 5.66 g of the desired product as a white solid, m.p. 114.5°–117° C. $[\alpha]_D^{20}-55.5$ (c 2 in CHCl$_3$).

Embodiment 4—Cyclo(D-phenylalanyl-D-histidine)

5.60 g of methyl ester of Embodiment 3 above was stirred and hydrogenated in 100 ml of methanol over 220 mg of 10% palladium on carbon at atmospheric pressure. After 3 hours, solids began to precipitate; an additional 25 ml of methanol was added to facilitate stirring. After 7 hours, an additional 280 ml of methanol was added as the mixture was heated to reflux. The mixture was filtered hot, and the filtrate was stripped to a gel-mush and mixed with 100 ml of diethyl ether. The resulting solid was filtered, washed with diethyl ether, and dried by suction and then under high vacuum at 35° C. to give 3.29 g of the desired product as an off-white powder, $[\alpha]_D^{23}=+68.5$ (c 2.0 in CH$_3$COOH).

Embodiment 5—(4-Chlorophenyl)isopropylketene

To a solution of 2.31 g of isopropyl(4-chlorophenyl)acetyl chloride in 10 ml of methylene chloride was added in one portion 1.5 g of triethylamine. After 18 hours, 15 ml of heptane was added to the mixture and the triethylamine hydrochloride removed by filtration. The filtrate was stripped and 10 ml of heptane was added and the resulting mixture was filtered and stripped to give a yellow residue, which was dissolved in 5 ml heptane for GLC analysis. The resulting solution was distilled through a Bantam-ware short-neck head from an oil bath at 125°–150° C. and head temperature of 110°–100° C. at 0.2–0.05 mm to give 0.95 g of distillate and 0.81 g of gum. The distillate was crystallized twice from 2 volumes of hexane at −80° C. The solid was melted and stripped to about 40° C. at 0.5 mm to give 0.42 g of the desired product as a yellow liquid.

Embodiment 6—(4-Chlorophenyl)isopropylketene

A sample of 53.2 g of isopropyl (4-chlorophenyl)acetic acid was treated with 21.5 ml of thionyl chloride in a 500 ml flask and heated slowly to 80° C. and maintained at 80° C. for 20 minutes. The reaction product was allowed to stand at room temperature for 2 days. The volatiles were stripped to 75° C. at 0.5 mm Hg. The resulting yellow liquid was diluted with 250 ml of methylene chloride followed by addition of 38.0 g of triethylamine. The mixture was stirred until triethylamine hydrochloride began to precipitate after 30 minutes. After 16 hours, the reaction mixture was filtered and solid triethylamine hydrochloride was washed with heptane. Most of the solvent was stripped from the filtrate by rotary evaporation at 50° C. The residue was diluted with 75 ml of heptane and additional triethylamine hydrochloride was removed by filtration as above. The filtrate was restripped and rediluted with 75 ml heptane and refiltered with the aid of 25 ml of heptane. The filtrate was cooled in dry ice, seeded and crystallized. The resulting crystals were filtered with a filter stick and washed with chilled heptane. The filtered solids were melted, diluted with one-half volume heptane, crystallized at −80° C. and the collected solid was melted and stored at −80° C. The filtrate solution was warmed, stripped of most solvent, then distilled through a Bantam ware short path head at 0.05 to 0.06 mm Hg from an oil bath at 90°–120° C. Total distillate was 14.5 g collected as a bright yellow-orange liquid at a head temperature of 60°–85° C. The distillate was crystallized from an equal volume of pentane at −80° C., filtered and washed twice with heptane as above to give, on warming, a second melt. The stripped filtrates totalling 5.79 g were crystallized as above in a 6-inch test tube and the melt was recrystallized immediately as described above to give a third melt. The three melts were combined and stripped to 50° C. at 5 mm Hg to give 29.4 g of the desired ketene as a yellow liquid.

Embodiment 7—(4-Chlorophenyl)isopropylketene

To 57.75 g of isopropyl(4-chlorophenyl)acetyl chloride was added 69.4 ml of triethylamine. The mixture was allowed to stand overnight at 20° C. The resulting mushy solid was crushed, diluted with 300 ml of redistilled hexane and filtered. The solids were washed three times with 75 ml of hexane, filtered and dried by suction with calcium chloride dried air to give 32 g triethylamine hydrochloride. The combined hexane solutions of ketene slowly deposited additional solids; the mixture was let stand at room temperature overnight with the flask wrapped in aluminum foil and filtered again to give 0.75 g of additional solids. The solvent was removed from the filtrate by rotary evaporation, then taken briefly to 1 mm Hg. To the mixture was added 500 ml of hexane, and after refiltration, the filtrate was stripped to a yellow oil. This oil was distilled through a Bantam-ware short path head at 0.5 mm Hg to give 28.61 g of the desired ketene as a yellow liquid, $d^{20}$ 1.10.

Embodiment 8—(4-(Difluoromethoxy)phenyl)isopropylketene

Following procedures similar to those described in Embodiment 7 above, the desired product is prepared by treating isopropyl(p-(difluoromethoxy)phenyl)acetyl chloride with triethylamine.

Embodiment 9—S-Isopropyl-(4-chlorophenyl)acetic Acid

To a Bantamware flask maintained under a nitrogen atmosphere, and fitted with a magnetic stirrer was added 0.69 g of 98% formic acid containing 28 mg of cyclo[D-phenylalanyl-D-histidine]. A two-phase system formed on injection of 3 ml of toluene. Addition of 1 ml acetone produced a single phase. This solution was cooled with ice to 6° C. and 1.96 g of (4-chlorophenyl)isopropylketene was injected. The reaction mixture was stirred, allowed to warm to 23° C. over 20 minutes, then at ambient temperature for 12 hours, treated with 4 ml of 1N hydrochloric acid for 2½ hours, then extracted with diethyl ether. The ether phase was extracted twice with solutions of 1.5 g of potassium carbonate in 4 ml of water. The aqueous extract was acidified with concentrated hydrochloric acid and extracted three times with diethyl ether. The combined organic phases were dried over MgSO$_4$, filtered and stripped to give 1.82 g of the desired S-isopropyl-(4-chlorophenyl)acetic acid as a white solid, $[\alpha]_D^{20} = -5.47$.

What is claimed is:

1. A process for the preparation of an optically-active (mixed) anhydride of an optically-active (chiral) carboxylic acid which comprises treating a non-symmetrical ketene with carboxylic acid in the presence of an optically-active (chiral) tertiary amine catalyst.

2. A process according to claim 1 wherein the optically-active amine catalyst is a nitrogen-base-substituted amino acid, a di- or polypeptide thereof or the reaction product of about one mole or three moles of a ketene with one mole of the nitrogen-base-substituted amino acid or di- polypeptide thereof.

3. A process according to claim 1 wherein the optically-active amine catalyst is a moderate or weakly basic amine.

4. A process according to claim 1 which is conducted in the presence of a non-hydroxylic solvent.

5. A process according to claim 4 wherein the catalyst is histidine or a histidine-containing di- or polypeptide in which at least one of the histidyl-free N-H and free COOH groups is modified with a protecting group into the form of an amide, or an acid addition salt thereof, and ester group respectively; or the reaction product of one mole of a histidine or histidine-containing di- or polypeptide with from about one mole to about three moles of a ketene.

6. A process according to claim 5 wherein the histidine moiety in the catalyst is histidine, 3-methyl-histidine, 3-ethylhistidine, 3-propylhistidine, 3-benzylhistidine, 1-methyl-histidine, 1-ethylhistidine, 1-propylhistidine or 1-benzylhistidine.

7. A process according to claim 6 wherein the catalyst is a cyclic dipeptide containing a histidine moiety and an alanine moiety.

8. A process according to claim 4 wherein the catalyst is selected from histidine, alpha-methyl-histidine, 1-methyl-histidine, 3-methylhistidine, cyclo(histidyl-histidine), (benzyloxycarbonylalanyl)histidine methyl ester, cyclo(alanyl-histidine), cyclo(beta-phenylalanyl-histidine), histidine methyl ester hydrochloride, histidine ethyl ester dihydrochloride, anserine, cyclo(valyl-histidine), glycyl-histidine, cyclo(phenylalanylglycyl-histidine), cyclo(leucyl-histidine), cyclo(homophenylalanyl-histidine), cyclo(phenylalanyl-methylhistidine), N-alpha-(beta-naphthoyl)histidine, histidyl-alanine, histidyl-phenylalanamide hydrochloride, histidyl-beta-phenylalanine, cyclo(histidylproline) or cyclo(glycyl-histidine) or a reaction product thereof with a ketene.

9. A process according to claim 1 wherein the acid is an alkanoic acid containing from 1 to 4 carbon atoms.

10. A process according to claim 9 wherein the acid is formic acid or acetic acid.

11. A process according to claim 1 wherein the non-symmetrical ketene has the formula

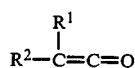

wherein $R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group each optionally ring substituted by one or more of halogen, alkyl, haloalkyl, alkoxy, haloalkoxy in which the halogens are bromine, chlorine or fluorine and the alkyl or cycloalkyl group contains 1 or 4 carbon atoms.

12. A process according to claim 11 wherein in the non-symmetrical ketene $R^1$ is isopropyl; $R^2$ is a phenyl group para-substituted by halogen, alkyl, haloalkoxy in which the halogen is chlorine or fluorine and the alkyl contain 1 to 4 carbon atoms.

13. A process according to claim 12 wherein the non-symmetrical ketene is (4-chlorophenyl)isopropylketene, (4-(difluoromethoxy)phenyl)isopropylketene, or ((4-(trifluoromethyl)-3-chlorophenyl)-(benzyloxycarbonyl)amino)isopropylketene.

14. A process according to claim 11 wherein the non-symmetrical ketene is prepared by treating an acid halide with a tertiary amine.

15. A process for the preparation of an optically-active carboxylic acid which comprises treating a non-symmetrical ketene with an optically-active or achiral carboxylic acid in the presence of an optically-active tertiary amine catalyst followed by separation of the resulting (mixed) anhydride diastereomers and hydrolysis of the resulting (mixed) anhydride diastereomer to the optically-active acid corresponding to the non-symmetrical ketene.

16. A process according to claim 15 wherein the optically-active amine catalyst is a nitrogen-base substituted amino acid, a di or polypeptide thereof or the reaction product of about one mole or three moles of a ketene with one mole of the nitrogen-base substituted amino acid or di- or polypeptide thereof.

17. A process according to claim 15 wherein the optically-active amine catalyst is a moderate or weakly basic amine.

18. A process according to claim 15 which is conducted in the presence of a non-hydroxylic solvent.

19. A process according to claim 18 wherein the catalyst is histidine or a histidine-containing di- or polypeptide in which at least one of the histidyl-free N-H and free COOH groups is modified with a protecting group into the form of an amide, or an acid addition salt thereof, and ester group respectively; or the reaction product of one mole of a histidine or histidine-containing di- or polypeptide with from about one mole to about three moles of a ketene.

20. A process according to claim 19 wherein the histidine moiety in the catalyst is histidine, 3-methyl-histidine, 3-ethylhistidine, 3-propyl-histidine, 3-benzylhistidine, 1-methylhistidine, 1-ethylhistidine, 1-propylhistidine or 1-benzylhistidine.

21. A process according to claim 20 wherein the catalyst is a cyclic dipeptide containing a histidine moiety and an alanine moiety.

22. A process according to claim 18 wherein the catalyst is optically active and selected from histidine, alpha-methyl-histidine, 1-methyl-histidine, 3-methylhistidine, cyclo(histidyl-histidine), (benzyloxycarbonylalanyl)-histidine methyl ester, cyclo(alanyl-histidine), cyclo(beta-phenylalanyl-histidine), histidine methyl ester hydrochloride, histidine ethyl ester dihydrochloride, anserine, cyclo(valyl-histidine), glycyl-histidine, cyclo(phenylalanyl-glycyl-histidine), cyclo(leucyl-histidine), cyclo(homophenylalanyl-histidine), cyclo(phenylalanyl-methylhistidine), N-alpha-(beta-naphthoyl)histidine, histidyl-alanine, histidyl-phenylalanamide hydrochloride, histidyl-beta-phenylalanine, cyclo(histidyl-proline) or cyclo(glycyl-histidine) or a reaction product thereof with a ketene.

23. A process according to claim 15 wherein the acid is an alkanoic acid containing from 1 to 4 carbon atoms.

24. A process according to claim 23 wherein the acid is formic acid or acetic acid.

25. A process according to claim 15 wherein the optically-active (mixed) anhydride is of formic or acetic and S-isopropyl-4-chloro-phenylacetic acids.

26. A process according to claim 15 wherein the non-symmetrical ketene has the formula

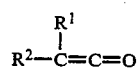

wherein $R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group each optionally ring substituted by one or more of halogen, alkyl, haloalkyl, alkoxy, haloalkoxy in which the halogens are bromine, chlorine or fluorine and the alkyl or cycloalkyl group contains 1 or 4 carbon atoms.

27. A process according to claim 26 wherein in the non-symmetrical ketene $R^1$ is isopropyl; $R^2$ is a phenyl group para-substituted by halogen, alkyl, haloalkoxy in which the halogen is chlorine or fluorine and the alkyl contain 1 to 4 carbon atoms.

28. A process according to claim 27 wherein the non-symmetrical ketene is (4-chlorophenyl)isopropylketene, (4-(difluoromethoxy)phenyl)isopropylketene, or ((4-(trifluoromethyl)-3-chlorophenyl)-(benzyloxycarbonyl)amino)isopropylketene.

29. A process according to claim 26 wherein the non-symmetrical ketene is prepared by treating an acid halide with a tertiary amine.

30. A process according to claim 29 wherein the acid halide is isopropyl-(4-chlorophenyl)acetyl chloride.

* * * * *